US012672897B2

(12) United States Patent
Desjardin et al.

(10) Patent No.: US 12,672,897 B2
(45) **Date of Patent: \*Jul. 7, 2026**

(54) SURGICAL ACCESS DEVICE INCLUDING DUAL LUMEN CANNULA FOR ANCHOR INFLATION AND DEFLATION

(71) Applicant: Covidien LP, Mansfield, MA (US)

(72) Inventors: Kevin Desjardin, Prospect, CT (US); Douglas M. Pattison, Bristol, CT (US); Oksana Buyda, Northford, CT (US); Christopher A. Tokarz, Wallingford, CT (US); Jason Mickus, Avon, CT (US); Astley C. Lobo, West Haven, CT (US); Amanda M. Adinolfi, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/018,980

(22) Filed: Jan. 13, 2025

(65) Prior Publication Data

US 2025/0143746 A1     May 8, 2025

Related U.S. Application Data

(63) Continuation of application No. 17/856,138, filed on Jul. 1, 2022, now Pat. No. 12,232,766, which is a continuation of application No. 16/869,773, filed on May 8, 2020, now Pat. No. 11,376,037.

(51) Int. Cl.
*A61B 17/34* (2006.01)

(52) U.S. Cl.
CPC .. *A61B 17/3423* (2013.01); *A61B 2017/3486* (2013.01); *A61B 17/3498* (2013.01)

(58) Field of Classification Search
CPC ............ A61B 17/3423; A61B 17/3498; A61B 2017/3486
See application file for complete search history.

(56) References Cited

U.S. PATENT DOCUMENTS

| | | | |
|---|---|---|---|
| 2018/0021489 A1* | 1/2018 | Yarger | A61M 1/84 604/541 |
| 2018/0271557 A1* | 9/2018 | Buyda | A61B 17/3423 |
| 2019/0059937 A1* | 2/2019 | Buyda | A61B 17/3423 |

\* cited by examiner

*Primary Examiner* — Tracy L Kamikawa
(74) *Attorney, Agent, or Firm* — Dymera IP, LLC

(57) ABSTRACT

A surgical access assembly includes a cannula including an elongated shaft having a proximal end portion including an anchor inflation port and a distal end portion including an expandable anchor. The elongated shaft includes an inner tube and an outer tube disposed over the inner tube. The inner tube includes at least one groove defined in an outer surface thereof that forms an inflation channel with an inner surface of the outer tube. The inflation channel is in communication with the anchor inflation port and the expandable anchor.

20 Claims, 6 Drawing Sheets

SURGICAL ACCESS DEVICE INCLUDING DUAL LUMEN CANNULA FOR ANCHOR INFLATION AND DEFLATION

CROSS-REFERENCE TO RELATED APPLICATIONS

This application is a continuation of U.S. patent application Ser. No. 17/856,138, filed Jul. 1, 2022, now U.S. Pat. No. 12,232,766, which is a continuation of U.S. patent application Ser. No. 16/869,773, filed May 8, 2020, now U.S. Pat. No. 11,376,037, the entire disclosures of which are incorporated herein by reference in their entireties. To the extent appropriate, a claim of priority is made to each of the above disclosed applications.

FIELD

The present disclosure relates generally to surgical access devices. In particular, the present disclosure relates to a dual lumen cannula of a surgical access device for inflating and deflating an expandable anchor of the surgical access device.

BACKGROUND

In minimally invasive surgical procedures, including endoscopic and laparoscopic surgeries, a surgical access device permits the introduction of a variety of surgical instruments into a body cavity or opening. A surgical access device (e.g., a cannula or an access port) is introduced through an opening in tissue (e.g., a naturally occurring orifice or an incision) to provide access to an underlying surgical site in the body. The opening is typically made using an obturator having a blunt or sharp tip that may be inserted through a passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instruments through the surgical access device to perform the surgical procedure.

Minimally invasive surgical procedures, including both endoscopic and laparoscopic procedures, permit surgery to be performed on organs, tissues, and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula into the abdominal cavity to perform one or more surgical tasks. The cannula may incorporate a seal to establish a substantially fluid tight seal about the laparoscopic instrument to preserve the integrity of the pneumoperitoneum. The cannula, which is subjected to the pressurized environment, e.g., the pneumoperitoneum, may include an anchor to prevent the cannula from backing out of the opening in the abdominal wall, for example, during withdrawal of the laparoscopic instrument from the cannula.

SUMMARY

This disclosure generally relates to a cannula for inflating and deflating an expandable anchor of a surgical access device. The cannula includes an inner tube having grooves defined in an outer surface thereof, and an outer tube disposed around the inner tube. Together, the grooves of the inner tube and an inner surface of the outer tube define lumens extending through the cannula. By incorporating the grooves in the outer surface of the inner tube, instead of forming a separate lumen between the inner and outer tubes, the number of components and assembly steps required to form the cannula is reduced, as well as the assembly time and/or material costs. Additionally, the grooves minimize the occurrence of the lumen and/or expandable anchor collapsing, for example, during deflation, and closing the fluid flow pathway, as compared to cannulas having the separate lumen formed between the inner and outer tubes.

In one aspect, the disclosure provides a surgical access assembly including a cannula having an elongated shaft including a proximal end portion including an anchor inflation port and a distal end portion including an expandable anchor. The elongated shaft includes an inner tube and an outer tube disposed over the inner tube. The inner tube includes at least one groove defined in an outer surface thereof that forms an inflation channel with an inner surface of the outer tube. The inflation channel is in communication with the anchor inflation port and the expandable anchor.

The at least one groove of the inner tube may include a proximal end in fluid communication with the anchor inflation port. The anchor inflation port may include a housing defining a cavity therein, and the proximal end of the at least one groove may be disposed within the cavity of the anchor inflation port. The anchor inflation port may include a collar extending from the housing and disposed around the elongated shaft. A proximal end of the outer tube may be disposed distal to the proximal end of the at least one groove of the inner tube.

The at least one groove of the inner tube may include a distal end in fluid communication with the expandable anchor. The expandable anchor may be coupled to the outer tube, and the outer tube may include an opening in communication with the distal end of the at least one groove of the inner tube and the expandable anchor.

The at least one groove of the inner tube may extend longitudinally along a length of the inner tube. The at least one groove may have a substantially rectangular shape. The at least one groove may include first and second walls disposed in substantially parallel relationship relative to each other, and a third wall interconnecting the first and second walls within a notched section of the at least one groove. The first wall may extend outwardly beyond the second wall, radially beyond the notched section of the at least one groove.

The inner surface of the outer tube may abut the outer surface of the inner tube.

The inner tube may include two grooves defined in the outer surface of the inner tube. The two grooves of the outer tube may extend longitudinally along a length of the inner tube in spaced relation relative to each other.

The expandable anchor may be a balloon.

The surgical access assembly may further include an instrument housing coupled to the proximal end portion of the cannula. The instrument housing may be disposed proximally of the anchor inflation port.

The surgical access assembly may further include a retention collar movably positioned along the elongated shaft of the cannula.

In another aspect, the disclosure provides a cannula including an elongated shaft including a proximal end portion including an anchor inflation port and a distal end portion including an expandable anchor. The elongated shaft includes an inner tube and an outer tube disposed over the inner tube. The inner tube includes an outer surface having at least one groove defined therein. An inner surface of the outer tube and the at least one groove in the outer surface of the inner tube define an inflation channel. The inflation channel is in communication with the anchor inflation port and the expandable anchor.

The details of one or more aspects of the disclosure are set forth in the accompanying drawings and the description below. Other features, objects, and advantages of the aspects described in this disclosure will be apparent from the description and drawings, and from the claims.

DETAILED DESCRIPTION

Figure 1:
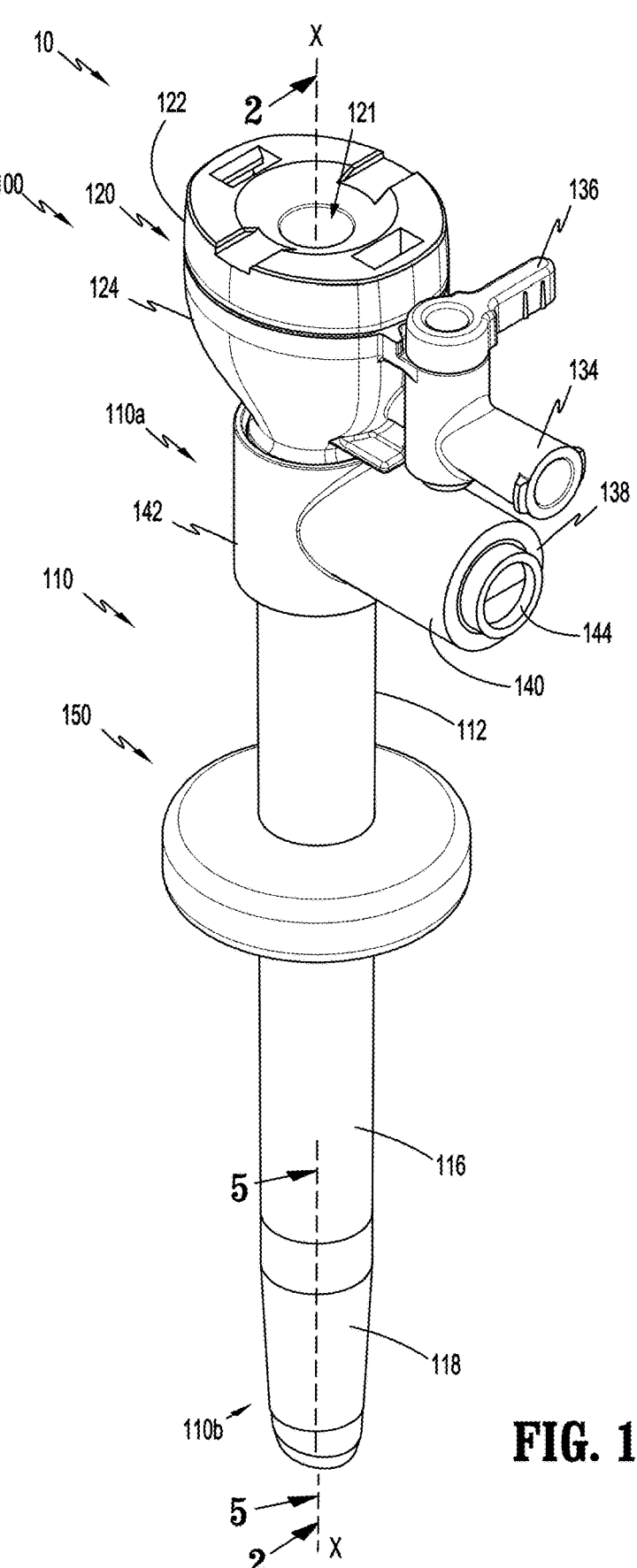
FIG. 1 is a perspective view of a surgical access assembly in accordance with an aspect of the disclosure.

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Like reference numerals refer to similar or identical elements throughout the description of the figures. Throughout this description, the term "proximal" refers to a portion of a structure, or component thereof, that is closer to a user, and the term "distal" refers to a portion of the structure, or component thereof, that is farther from the user.

Surgical access assemblies with obturators, known as trocar assemblies, are employed during minimally invasive surgery, e.g., laparoscopic surgery, and provide for the sealed access of surgical instruments into an insufflated body cavity, such as the abdominal cavity. The surgical access assemblies of the present disclosure include an instrument housing mounted on a cannula. An obturator (not shown) is insertable through the instrument housing and the cannula. The obturator can have a blunt distal end, or a bladed or non-bladed penetrating distal end, and can be used to incise and/or separate tissue of the abdominal wall so that the surgical access assembly can be introduced into the abdomen. The handle of the obturator can engage or selectively lock into the instrument housing of the surgical access assembly.

Trocar assemblies are employed to tunnel through an anatomical structure, e.g., the abdominal wall, either by making a new passage through the anatomical structure or by passing through an existing opening through the anatomical structure. Once the surgical access assembly with the obturator has tunneled through the anatomical structure, the obturator is removed, leaving the surgical access assembly in place. The instrument housing of the surgical access assembly includes valves and/or seals that prevent the escape of insufflation fluid from the body cavity, while also allowing surgical instruments to be inserted into the body cavity.

In various aspects, a bladeless optical trocar obturator may be provided that permits separation of tissue planes in a surgical procedure and visualization of body tissue fibers as they are being separated, thereby permitting a controlled traversal across a body wall. In other aspects, the trocar obturator may be bladeless without being optical, e.g., without providing contemporaneous visualization thereof through the distal tip of the trocar obturator. The bladeless trocar obturator may be provided for the blunt dissection of the abdominal lining during a surgical procedure.

Various trocar obturators suitable for use with the surgical access assembly of the present disclosure are known and include, for example, bladed, bladeless, blunt, optical, and non-optical. For a detailed description of the structure and function of exemplary trocar assemblies, including exemplar trocar obturators and exemplar cannulas, please refer to PCT Publication No. WO 2016/186905, the entire content of which is hereby incorporated by reference herein.

Figure 2:
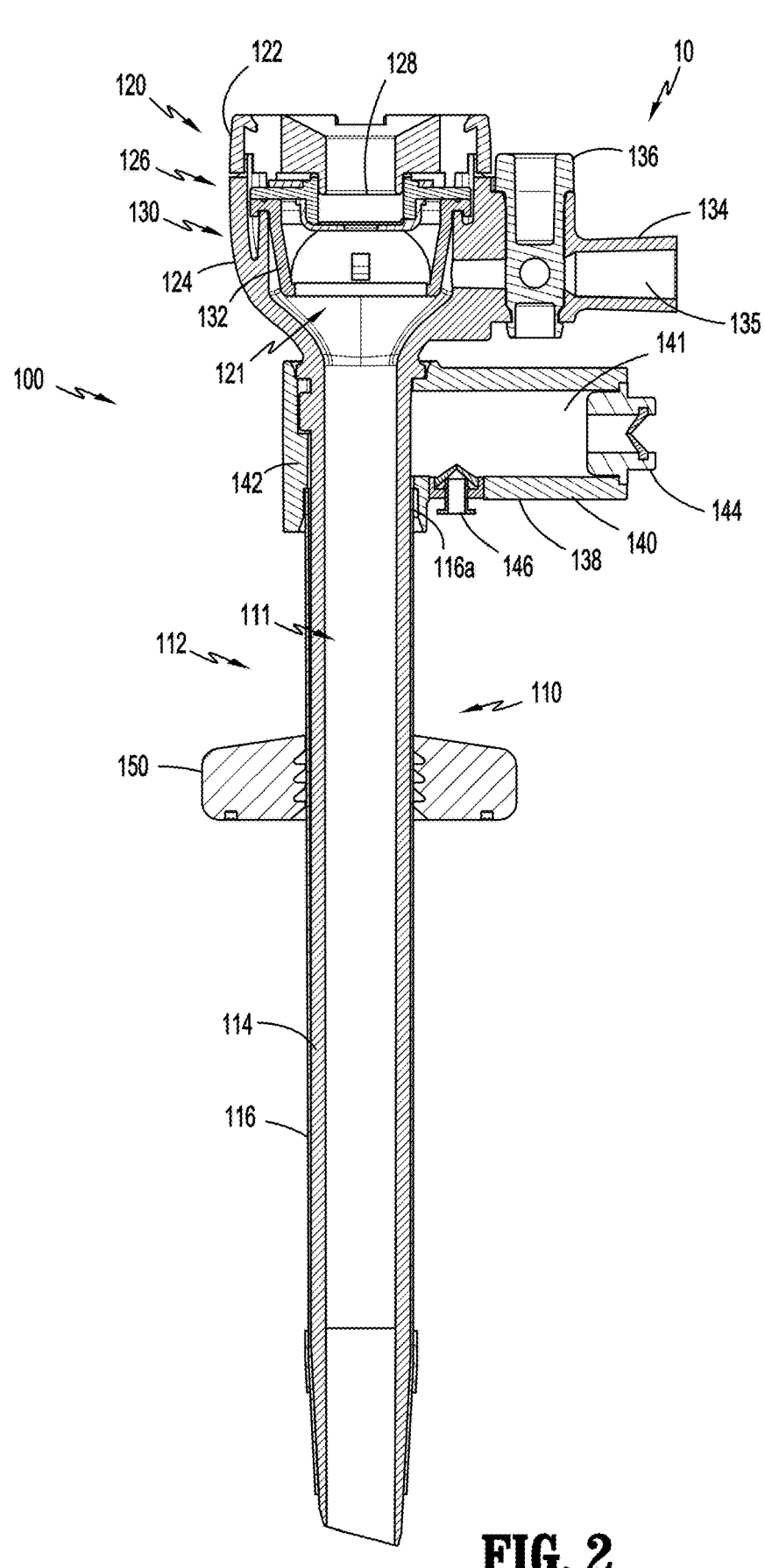
FIG. 2 is cross-sectional view of the surgical access assembly of FIG. 1, taken along section line 2-2 of FIG. 1.

FIGS. 1 and 2 illustrates a surgical access assembly 10 including a surgical access device 100 and a retention collar 150 supported on the surgical access device 100. The surgical access assembly 10 will further be described to the extent necessary to disclose aspects of the disclosure. For a detailed description of the structure and function of exemplary surgical access devices and/or retention collars, reference may be made to U.S. Pat. Nos. 7,300,448; 7,691,089; and 8,926,508, the entire content of each of which is hereby incorporated by reference herein. Accordingly, it should be understood that a variety of surgical access assemblies may be utilized with a cannula of the present disclosure.

The surgical access device 100 includes a cannula 110 and an instrument housing 120 secured to the cannula 110. The cannula 110 generally includes an elongated shaft 112 extending along a longitudinal axis "X" and defining an access lumen 111 for reception and passage of a surgical instrument (not shown) therethrough. The elongated shaft 112 includes an inner tube 114 and an outer tube 116 coaxially mounted over the inner tube 114. A proximal end portion 110a of the cannula 110 supports the instrument housing 120 thereon and a distal end portion 110b of the cannula 110 supports an expandable anchor 118 (e.g., an inflatable anchor, such as a balloon, or a contractable anchor, such as a collapsible flange). More particularly, the expandable anchor 118 is operably coupled to the outer tube 116. The expandable anchor 118 secures the cannula 110 against an inner surface of a body wall, such as an abdominal wall (see FIG. 6).

The retention collar 150 is supported on the elongated shaft 112 of the cannula 110. The retention collar 150 is releasably engageable with the elongated shaft 112, and slidable therealong to adjust the longitudinal position of the retention collar 150 on the elongated shaft 112. The retention collar 150 secures the cannula 110 against an outer surface of a body wall (see e.g., FIG. 6). The retention collar 150 may be formed from a compressible material to aid in sealing the opening into the tissue of the body wall. The retention collar 150 may include any known retention mechanism used on cannulas and/or trocars, such as foam collars and/or suture ties.

The instrument housing 120 includes an upper housing section 122 and a lower housing section 124, and defines a cavity 121 therein that communicates with the access lumen 111 of the elongated shaft 112 of the cannula 110. The upper housing section 122 may be selectively attachable to, and detachable from, the lower housing section 124, or the upper housing section 122 may be permanently attached to the lower housing section 124 (e.g., via welding, adhesives, etc.). The lower housing section 124 may be releasably or permanently attached to the elongated shaft 112 (e.g., the inner tube 114) of the cannula 110. In aspects, either or both of the upper and lower housing sections 122, 124 of the instrument housing 120 may include knurls, indentations, tabs, or be otherwise configured to facilitate engagement by a user.

The instrument housing 120 supports a seal assembly 126 and a valve assembly 130 therein. The seal assembly 126 is disposed proximally of the valve assembly 130. The seal assembly 126 generally includes an instrument seal 128 for sealing around surgical instruments (not shown) inserted into the cannula 110, and the valve assembly 130 generally includes a zero-closure seal 132 for sealing the access lumen 111 of the cannula 110 in the absence of a surgical instrument inserted through the cannula 110. The seal assembly 126 and the valve assembly 130 prevent the escape of the insufflation fluid therefrom, while allowing surgical instruments to be inserted therethrough and into the body cavity. The instrument seal 128 may include any known instrument seal used in cannulas and/or trocars, such as septum seal. The zero-closure seal 132 may be any known zero-closure seal for closing off the passageway into the access lumen 111, such as a duckbill seal or flapper valve.

The instrument housing 120 includes an insufflation port 134 coupled to the lower housing section 124. The insufflation port 134 defines an opening 135 therethrough that is in fluid communication with the cavity 121 of the instrument housing 120 which, in turn, is in fluid communication with the access lumen 111 of the cannula 110 to insufflate a body cavity, such as abdominal cavity (e.g., create a pneumoperitoneum). The opening 135 of the insufflation port 134 is disposed distally of the valve assembly 130 to maintain insufflation pressure within the body cavity. The insufflation port 134 is connectable to a source of insufflation fluid (not shown) for delivery of the insufflation fluid (e.g., gases) into the body cavity. The insufflation port 134 is configured and dimensioned to receive a valve 136 in a substantially fluid-tight manner. In aspects, and as shown, the valve 136 is a stopcock valve for controlling the flow of the insufflation fluid. The valve 136, however, may be any known valve for directing fluid flow and, in some aspects, regulating fluid flow.

The cannula 110 includes an anchor inflation port 138 coupled to the elongated shaft 112 (e.g., via adhesives or solvent bond). The anchor inflation port 138 includes a housing 140 and a collar 142 extending from the housing 140. The collar 142 secures the housing 140 to the elongated shaft 112. The collar 142 extends around the elongated shaft 112 and is engaged with the elongated shaft 112 in a manner that fixes (e.g., longitudinally and rotationally) the anchor inflation port 138 relative to the elongated shaft 112. More particularly, the collar 142 is engaged with the inner tube 114 of the elongated shaft 112 by snap fit connection, and is further seated over a proximal end 116a of the outer tube 116, for example, in a friction fit manner. It should be understood that other mating structures and relationships may be utilized to secure the anchor inflation port 138 to the elongated shaft 112.

The anchor inflation port 138 is in fluid communication with the expandable anchor 118. The housing 140 of the anchor inflation port 138 defines a cavity 141 therein that is in fluid communication with inflation lumens or channels 143 (FIG. 5) of the cannula 110 which, in turn, is in fluid communication with the expandable anchor 118, as described in detail below. The housing 140 is connectable to a fluid source (not shown) for delivery of a fluid (e.g., gases) into the expandable anchor 118. The anchor inflation port 138 includes an inlet valve 144 and an outlet valve 146 operably coupled to the housing 140 in a substantially fluid-tight manner. In aspects, and as shown, the inlet valve 144 is a check valve that allows the fluid to flow into the expandable anchor 118 and prevents reverse flow of the fluid therefrom, and the outlet valve 146 is a release valve that allows the escape of the fluid from the expandable anchor 118. The inlet and outlet valves 144, 146, however, may be any known valves for controlling fluid flow and, in some aspects, the anchor inflation port 138 may include a single valve for delivery and removal of fluid into and out of the expandable anchor 118. For example, a syringe (not shown) may be coupled to the inlet valve 144 (e.g., a tip of the syringe may be positioned through the inlet valve) to deliver air into the expandable anchor 118 or to remove air from the expandable anchor 118. In some aspects, the anchor inflation port 138 may further include a relief valve (not shown) to limit the pressure that can build up in the expandable anchor 118.

Figure 3:
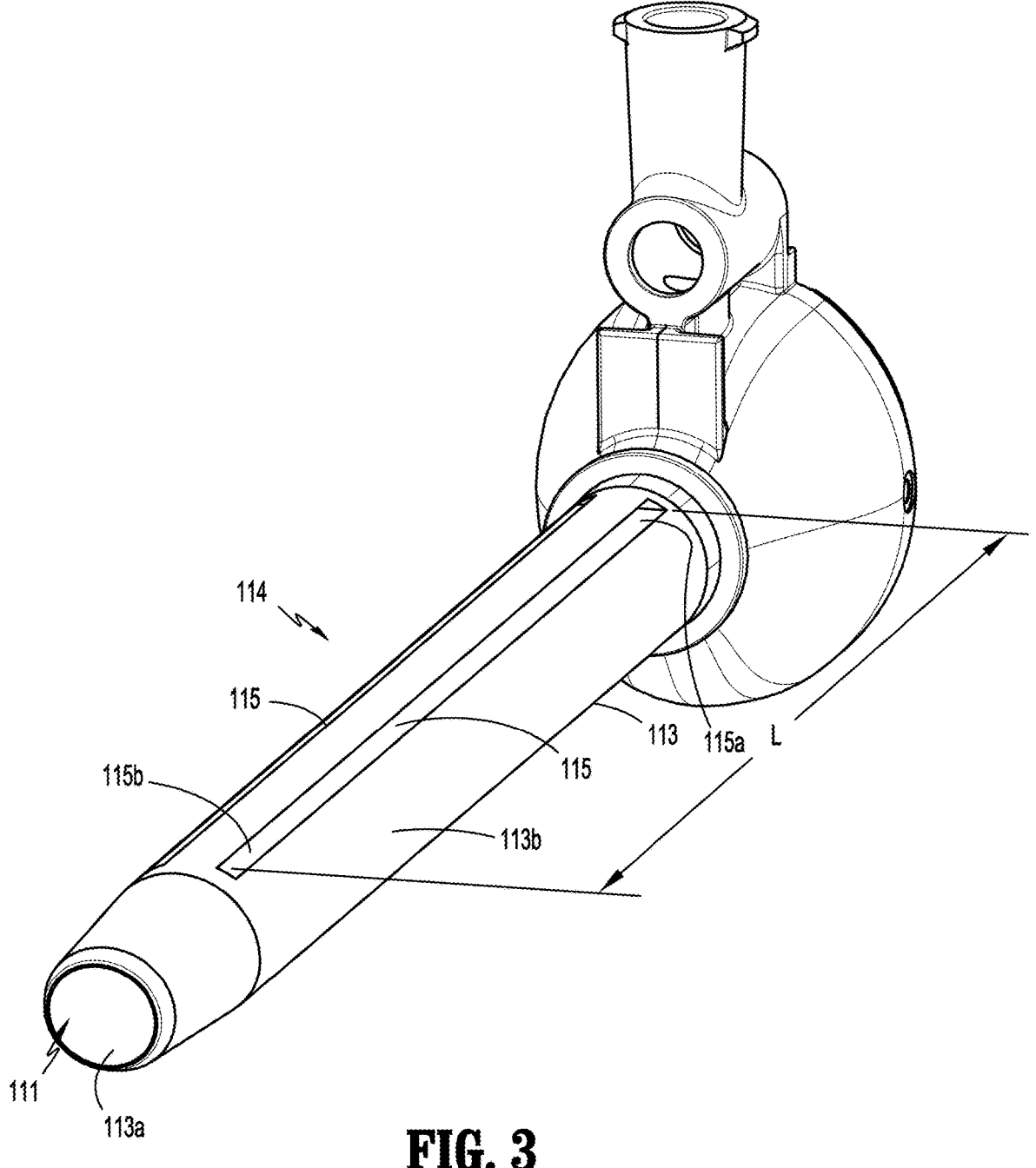
FIG. 3 is a perspective view of an inner tube of a cannula of the surgical access assembly of FIG. 1.
Figure 4:
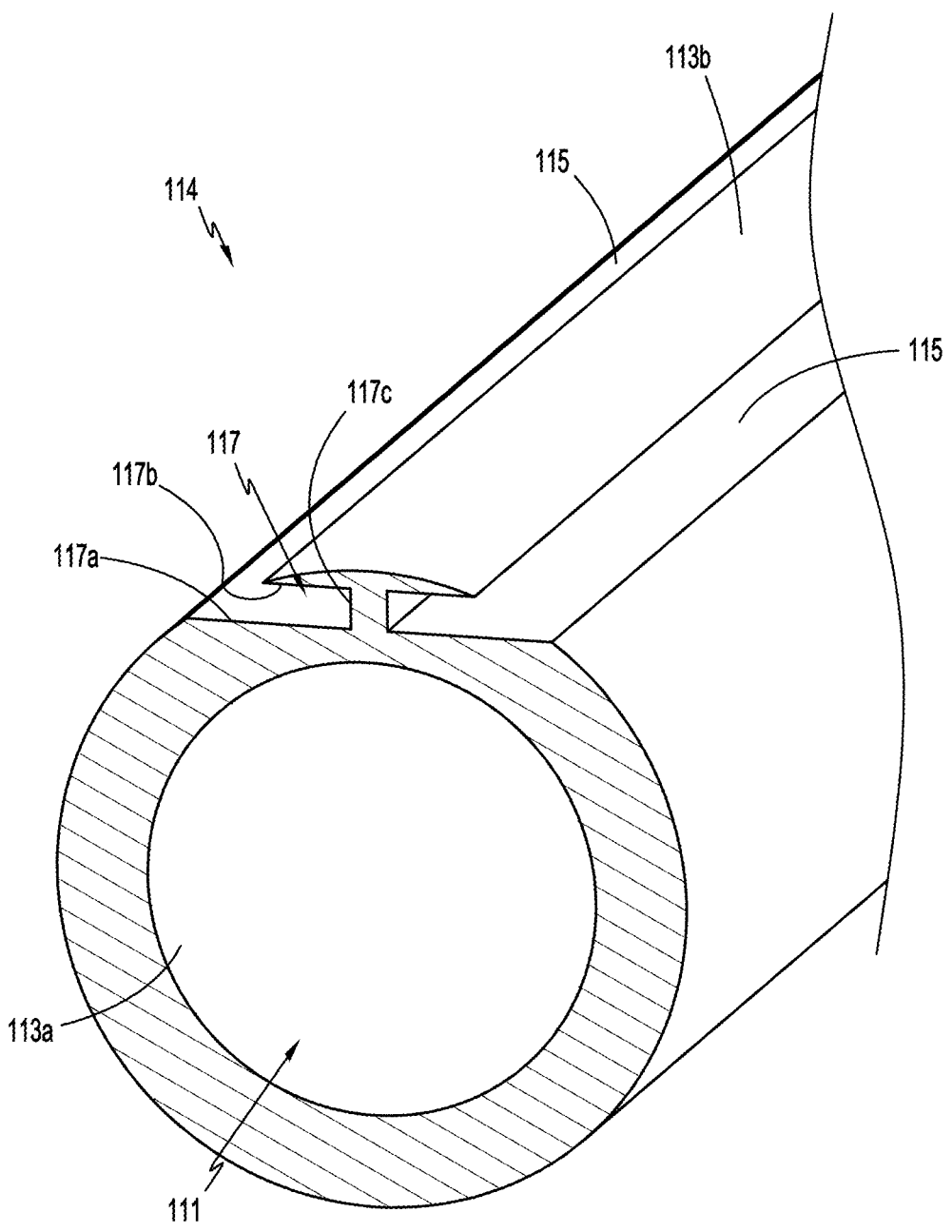
FIG. 4 is a perspective view of a portion of the inner tube of FIG. 3.

Turning now to FIGS. 3 and 4, the inner tube 114 of the cannula 110 has a cylindrical body 113 includes an inner surface 113a defining the access lumen 111 of the elongated shaft 112 and an outer surface 113b having a generally annular shape with grooves 115 defined therein. The grooves 115 extend longitudinally along a length "L" of the inner tube 114 between a proximal end 115a and a distal end 115b. The grooves 115 are disposed in radial spaced relation relative to each other.

Each groove 115 is substantially rectangular in shape and includes first and second walls 117a, 117b that are substantially planar and disposed in substantially parallel relationship relative to each other. A third wall 117c interconnects the first and second walls 117a, 117b. The third wall 117c is substantially planar and disposed substantially orthogonal to the first and second walls 117a, 117b. Together, the first, second, and third walls 117a, 117b, 117c define a notched section 117 of the groove 115. The first wall 117a extends outwardly beyond the second wall 117c, radially outwardly of the notched section 117. The grooves 115 may be formed by cutting the outer surface 113b of the inner tube 114, or the inner tube 114 may be molded to include the grooves 115.

It should be understood that the grooves 115 may have other sizes and/or shapes. It should be further understood that the number of grooves 115 defined in the outer surface 113b of the inner tube 114 may vary. In some aspects, the inner tube 114 may include a plurality of grooves 115 or sets of grooves 115 radially dispersed around the inner tube 114.

Figure 5:
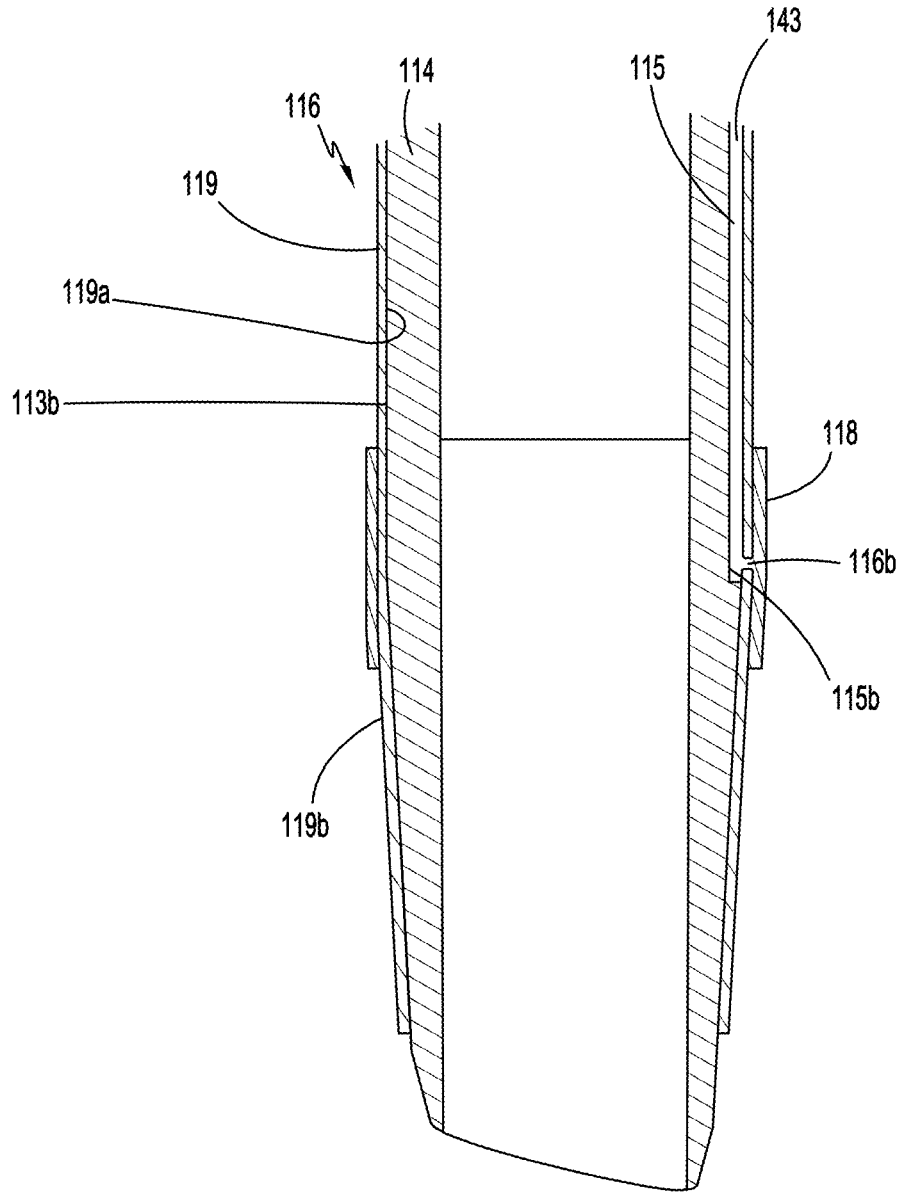
FIG. 5 is a cross-sectional view of the surgical access assembly of FIG. 1, taken along section line 5-5 of FIG. 1.

As shown in FIGS. 2 and 5, the outer tube 116 has a cylindrical body 119 including an inner surface 119a abutting the outer surface 113b of the inner tube 114 and an outer surface 119b configured to engage tissue. Together, the inner and outer tubes 114, 116 form the inflation channels 143 through the cannula 110. More particularly, the inflation channels 143 are defined between the grooves 115 (FIG. 3) of the inner tube 114 and the inner surface 119a of the outer tube 116.

The inflation channels 143 provide a pathway for fluid flow from the fluid source (not shown) to the expandable anchor 118. The grooves 115 define a rigid fluid pathway in contrast to the use of a separate lumen (e.g., a catheter tube)

that is susceptible to collapsing or becoming constricted. The proximal end 115a of each groove 115 is disposed within the cavity 141 of the housing 140 of the anchor inflation port 138 to provide an inlet from the fluid source (not shown) during inflation and an outlet into the cavity 141 during deflation. The distal end 115b of each groove 115 is disposed within the expandable anchor 118 and in communication therewith via, for example, an opening 116b extending through the outer tube 116, to provide an inlet into the expandable anchor 118 during inflation and an outlet from the expandable anchor 118 during deflation. It should be understood that the outer tube 116 and the expandable anchor 118 are secured (e.g., glued and/or welded) together to create hermetic contact therebetween, or may be formed (e.g., blow molded) as a single piece.

To inflate the expandable anchor 118, a fluid source (not shown) is releasably attached to the anchor inflation port 138 and pressurized fluid is introduced into the anchor inflation port 138, through the inflation channels 143, and into the expandable anchor 118 causing the expandable anchor 118 to expand. To deflate the expandable anchor 118, the outlet valve 146 of the anchor inflation port 138 is actuated to depressurize the fluid and allow it to escape therethrough causing the expandable anchor 118 to retract or collapse.

Figure 6:
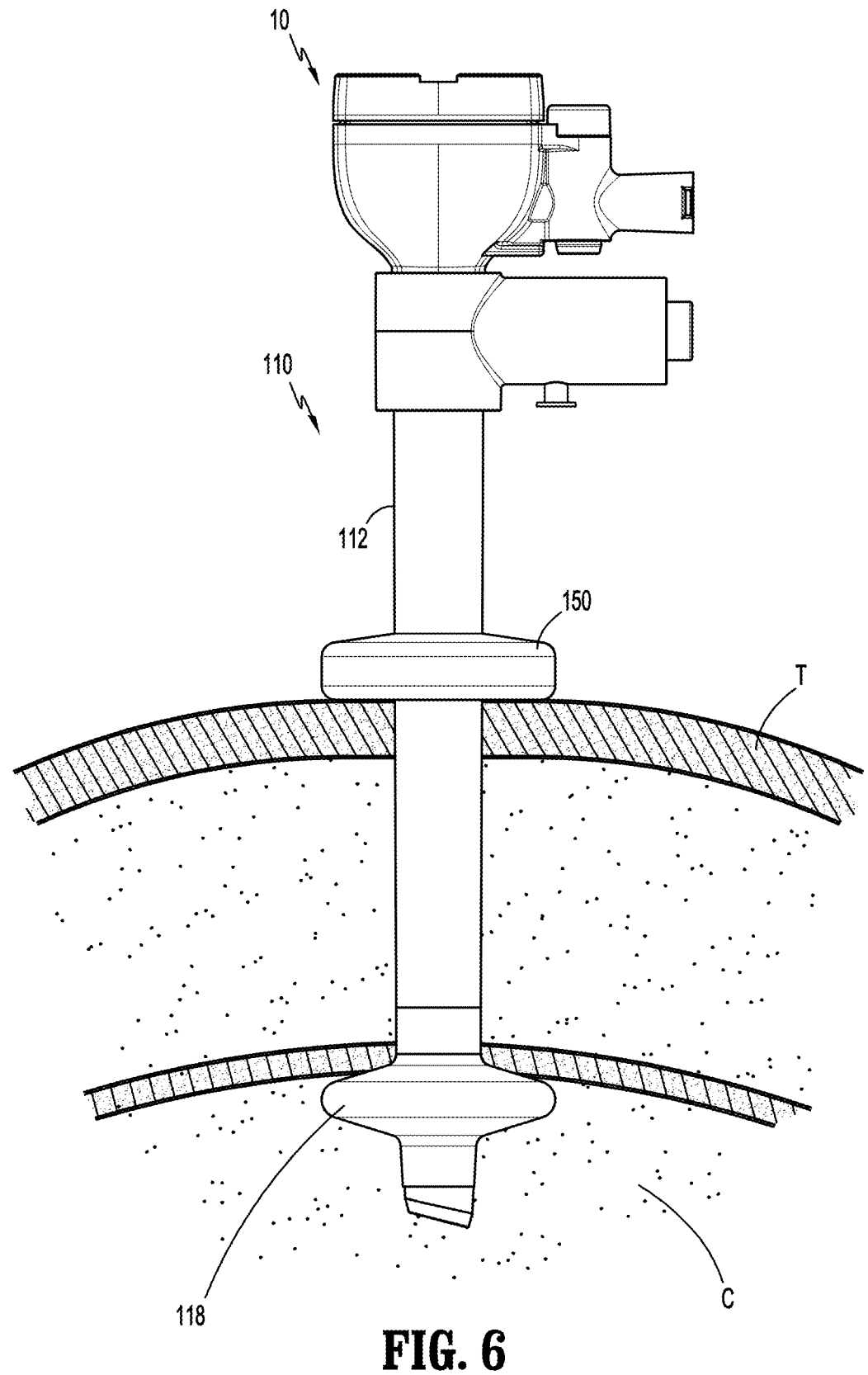
FIG. 6 is a side view of the surgical access assembly of FIG. 1, shown secured to tissue.

FIG. 6 illustrates the surgical access assembly 10 disposed within tissue "T," e.g., an abdominal wall. The elongated shaft 112 of the cannula 110 is received through the tissue "T" (e.g., by utilizing an obturator (not shown) to facilitate entry of the cannula 110 through the tissue "T"), and the expandable anchor 118 is inflated within a body cavity "C" to prevent the cannula 110 from being withdrawn through the tissue "T." The retention collar 150 is slid distally along the elongated shaft 112 of the cannula 110 until the retention collar 150 abuts or presses on the tissue "T." The tissue "T" is thus sandwiched between the expandable anchor 118 and the retention collar 150 to prevent the cannula 110 from being withdrawn from or over-inserted into the tissue "T." In this manner, the surgical access assembly 10 is secured to the tissue "T" and longitudinal movement of the cannula 110 relative to the tissue "T" is prevented or minimized throughout insertion, withdrawal, and/or manipulation of a surgical instrument (not shown) through the cannula 110. Following the surgical procedure, the expandable anchor 118 is deflated to permit the withdrawal of the surgical access assembly 10 from the tissue "T."

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Therefore, the above description should not be construed as limiting, but merely as exemplifications of aspects of the disclosure. Thus, the scope of the disclosure should be determined by the appended claims and their legal equivalents, rather than by the examples given.

What is claimed is:
1. A surgical access device comprising:
a cannula including an elongated shaft having a first inner surface and an outer surface, the first inner surface defining an access lumen through the elongated shaft;
a groove defined in the outer surface of the elongated shaft, the groove having:

a first wall and a second wall, the first wall and the second wall being substantially planar and substantially parallel to one another; and
a third wall interconnecting a first end of the first wall and a first end of the second wall, the third wall being substantially orthogonal to the first wall and the second wall and aligned along a plane that intersects the access lumen and the outer surface;
an outer tube disposed over the elongated shaft, the outer tube including a second inner surface interconnecting a second end of the first wall and a second end of the second wall; and
an inflation channel defined by the second inner surface and the groove.

2. The surgical access device of claim 1, further comprising:
an expandable anchor coupled to the elongated shaft and in fluid communication with the inflation channel.

3. The surgical access device of claim 2, wherein the inflation channel is configured to provide a pathway for fluid flow from a fluid source to the expandable anchor.

4. The surgical access device of claim 2, wherein the expandable anchor is positioned around a distal end portion of the elongated shaft, and a distal end of the inflation channel is in communication with the expandable anchor via an opening extending through the outer tube.

5. The surgical access device of claim 2, wherein the expandable anchor is a balloon.

6. The surgical access device of claim 1, further comprising:
an anchor inflation port coupled to the elongated shaft and in fluid communication with the inflation channel.

7. The surgical access device of claim 6, wherein the anchor inflation port defines a cavity, and a proximal end of the inflation channel is disposed within the cavity.

8. The surgical access device of claim 1, wherein the inflation channel is one of a plurality of inflation channels defined in the elongated shaft.

9. The surgical access device of claim 1, wherein the first wall extends beyond the second wall.

10. The surgical access device of claim 1, wherein the first wall, the second wall, and the third wall of the groove are substantially planar, and wherein a fourth wall formed by the second inner surface is curved.

11. The surgical access device of claim 1, wherein a distance between the first end of the first wall and the first end of the second wall is less than a distance between the second end of the first wall and the second end of the second wall.

12. A surgical access device comprising:
an elongated shaft having a first inner surface and an outer surface, the first inner surface defining an access lumen through the elongated shaft;
grooves defined in the outer surface of the elongated shaft, each groove having:
a first wall and a second wall, the first wall being aligned along a first axis and substantially parallel to the second wall; and
a third wall interconnecting a first end of the first wall and a first end of the second wall, the third wall being aligned along a second axis and substantially orthogonal to the first wall and the second wall, wherein the second axis intersects the access lumen and the outer surface;
an outer tube disposed over the elongated shaft, the outer tube including a second inner surface; and

inflation channels defined by each groove and a respective portion of the second inner surface, each respective portion of the second inner surface interconnecting a second end of the first wall and a second end of the second wall of each groove.

13. The surgical access device of claim 12, further comprising:

an expandable anchor coupled to the elongated shaft and in fluid communication with the inflation channels.

14. The surgical access device of claim 13, wherein the inflation channels are configured to provide pathways for fluid flow from a fluid source to the expandable anchor.

15. The surgical access device of claim 13, wherein the expandable anchor is positioned around a distal end portion of the elongated shaft, and wherein distal ends of the inflation channels are in communication with the expandable anchor via openings extending through the outer tube.

16. The surgical access device of claim 12, wherein the inflation channels are disposed adjacent to one another within the elongated shaft.

17. The surgical access device of claim 12, wherein each groove further comprises a fourth wall formed by the respective portion of the second inner surface interconnecting the second end of the first wall and the second end of the second wall.

18. The surgical access device of claim 12, further comprising:

an anchor inflation port coupled to the elongated shaft and in fluid communication with the inflation channels.

19. The surgical access device of claim 18, wherein the anchor inflation port defines a cavity, and proximal ends of the inflation channels are disposed within the cavity.

20. A surgical access device comprising:

a cannula including an elongated shaft having a first inner surface and an outer surface, the first inner surface defining an access lumen through the elongated shaft;

a groove defined in the outer surface of the elongated shaft, the groove having:

a first wall and a second wall, the first wall and the second wall being substantially planar and substantially parallel to one another, wherein the first wall and the second wall are each aligned along a respective plane that does not intersect the access lumen; and a third wall interconnecting a first end of the first wall and a first end of the second wall, the third wall being substantially orthogonal to the first wall and the second wall and aligned along a plane that intersects the access lumen and the outer surface;

an outer tube disposed over the elongated shaft, the outer tube including a second inner surface interconnecting a second end of the first wall and a second end of the second wall;

an inflation channel defined by the second inner surface and the groove; and an expandable anchor coupled to the elongated shaft and in fluid communication with the inflation channel.

* * * * *